(12) United States Patent
Chan et al.

(10) Patent No.: US 8,801,727 B2
(45) Date of Patent: Aug. 12, 2014

(54) ORTHOPEDIC SUTURE PASSER AND METHOD

(75) Inventors: Kwan-Ho Chan, Singapore (SG); M. Mary Sinnott, Logan, UT (US); Patrick Michel White, West Chester, PA (US)

(73) Assignee: Smith & Nephew, Inc., Memphis, TN (US)

( * ) Notice: Subject to any disclaimer, the term of this patent is extended or adjusted under 35 U.S.C. 154(b) by 101 days.

(21) Appl. No.: 13/527,765

(22) Filed: Jun. 20, 2012

(65) Prior Publication Data
US 2013/0012953 A1 Jan. 10, 2013

Related U.S. Application Data

(60) Provisional application No. 61/568,137, filed on Dec. 7, 2011, provisional application No. 61/505,992, filed on Jul. 8, 2011, provisional application No. 61/506,000, filed on Jul. 8, 2011, provisional application No. 61/506,004, filed on Jul. 8, 2011.

(51) Int. Cl.
*A61B 17/58* (2006.01)
*A61B 17/60* (2006.01)
*A61F 2/00* (2006.01)

(52) U.S. Cl.
USPC .............................. 606/103; 606/88; 606/139

(58) Field of Classification Search
USPC .............................. 606/103, 88, 89, 139, 148
See application file for complete search history.

(56) References Cited

U.S. PATENT DOCUMENTS

| | | |
|---|---|---|
| 919,138 A | 4/1909 | Drake et al. |
| 1,037,864 A | 9/1912 | Carlson et al. |
| 1,449,087 A | 3/1923 | Bugbee |
| 1,635,066 A | 7/1927 | Wells |
| 1,815,725 A | 7/1931 | Pilling et al. |
| 1,822,330 A | 9/1931 | Ainslie |
| 1,856,721 A | 5/1932 | Nagelmann |
| 1,918,700 A | 7/1933 | Harris |
| 1,933,024 A | 10/1933 | Nagelmann |
| 1,981,651 A | 11/1934 | Logan |
| 2,240,330 A | 4/1941 | Flagg et al. |
| 2,269,963 A | 1/1942 | Wappler |
| 2,286,578 A | 6/1942 | Sauter |
| 2,291,413 A * | 7/1942 | Siebrandt ...................... 606/103 |
| 2,301,500 A | 11/1942 | Anderson |
| 2,577,240 A | 12/1951 | Findley |
| 2,697,433 A | 12/1954 | Zehnder |
| 2,738,790 A | 3/1956 | Todt, Sr. et al. |
| 3,013,559 A | 12/1961 | Thomas |
| 3,090,386 A | 5/1963 | Curtis |

(Continued)

FOREIGN PATENT DOCUMENTS

| | | |
|---|---|---|
| WO | WO03/007799 A2 | 1/2003 |
| WO | WO2004/002324 A1 | 1/2004 |

OTHER PUBLICATIONS

2008 Arthrex Inc., "The Arthrex Scorpion" 6 pages.

(Continued)

*Primary Examiner* — Andrew Yang
(74) *Attorney, Agent, or Firm* — David Chambers; David Warmbold

(57) ABSTRACT

Instruments and techniques to pass a suture are presented. In one illustrative example, a suture passer includes a drill guide and is able to form a tunnel in a bone and pass a suture through the tunnel so formed.

15 Claims, 19 Drawing Sheets

(56) References Cited

U.S. PATENT DOCUMENTS

| | | |
|---|---|---|
| 3,470,875 A | 10/1969 | Johnson |
| 3,638,653 A | 2/1972 | Berry |
| 3,840,017 A | 10/1974 | Violante |
| 3,842,840 A | 10/1974 | Schweizer |
| 3,946,740 A | 3/1976 | Bassett |
| 4,109,658 A | 8/1978 | Hughes |
| 4,164,225 A | 8/1979 | Johnson et al. |
| 4,172,458 A | 10/1979 | Pereyra |
| 4,224,947 A | 9/1980 | Fukuda |
| 4,345,601 A | 8/1982 | Fukuda |
| 4,373,530 A | 2/1983 | Kilejian |
| 4,406,237 A | 9/1983 | Eguchi et al. |
| 4,417,532 A | 11/1983 | Yasukata |
| 4,493,323 A | 1/1985 | Albright et al. |
| 4,596,249 A | 6/1986 | Freda et al. |
| 4,686,972 A | 8/1987 | Kurland |
| 4,739,751 A | 4/1988 | Sapega et al. |
| 4,781,182 A | 11/1988 | Purnell et al. |
| 4,823,780 A | 4/1989 | Odensten et al. |
| 4,836,205 A | 6/1989 | Barrett |
| 4,883,048 A | 11/1989 | Purnell et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 4,964,861 A | 10/1990 | Agee et al. |
| 5,059,201 A | 10/1991 | Asnis |
| 5,112,335 A | 5/1992 | Laboureau et al. |
| 5,112,337 A | 5/1992 | Paulos et al. |
| 5,217,471 A | 6/1993 | Burkhart |
| 5,222,977 A | 6/1993 | Esser |
| 5,281,237 A | 1/1994 | Gimpelson |
| 5,312,422 A | 5/1994 | Trott |
| 5,318,577 A | 6/1994 | Li |
| 5,336,229 A | 8/1994 | Noda |
| 5,397,325 A | 3/1995 | Della Badia et al. |
| 5,431,666 A | 7/1995 | Sauer et al. |
| 5,433,722 A | 7/1995 | Sharpe et al. |
| 5,439,467 A | 8/1995 | Benderev et al. |
| 5,454,823 A | 10/1995 | Richardson et al. |
| 5,462,562 A | 10/1995 | Elkus |
| 5,474,565 A | 12/1995 | Trott |
| 5,499,991 A | 3/1996 | Garman et al. |
| 5,520,693 A | 5/1996 | McGuire et al. |
| 5,522,820 A | 6/1996 | Caspari et al. |
| 5,544,664 A | 8/1996 | Benderev et al. |
| 5,562,664 A * | 10/1996 | Durlacher et al. .............. 606/96 |
| 5,562,686 A | 10/1996 | Sauer et al. |
| 5,571,119 A | 11/1996 | Atala |
| 5,573,542 A | 11/1996 | Stevens |
| 5,575,801 A | 11/1996 | Habermeyer et al. |
| 5,618,290 A | 4/1997 | Toy et al. |
| 5,632,752 A | 5/1997 | Buelna |
| 5,645,552 A | 7/1997 | Sherts |
| 5,662,663 A | 9/1997 | Shallman |
| 5,662,664 A | 9/1997 | Gordon et al. |
| 5,665,096 A | 9/1997 | Yoon |
| 5,690,653 A | 11/1997 | Richardson et al. |
| 5,713,908 A | 2/1998 | Jameel et al. |
| 5,713,910 A | 2/1998 | Gordon et al. |
| 5,730,747 A | 3/1998 | Ek et al. |
| 5,741,277 A | 4/1998 | Gordon et al. |
| 5,741,278 A | 4/1998 | Stevens |
| 5,741,279 A | 4/1998 | Gordon et al. |
| 5,741,281 A | 4/1998 | Martin |
| 5,766,186 A | 6/1998 | Faraz et al. |
| 5,776,150 A | 7/1998 | Nolan et al. |
| 5,792,153 A | 8/1998 | Swain et al. |
| 5,797,927 A | 8/1998 | Yoon |
| 5,860,992 A | 1/1999 | Daniel et al. |
| 5,871,488 A | 2/1999 | Tovey et al. |
| 5,902,311 A | 5/1999 | Andreas et al. |
| 5,904,692 A | 5/1999 | Steckel et al. |
| 5,908,426 A | 6/1999 | Pierce |
| 5,919,199 A | 7/1999 | Mers Kelly et al. |
| 5,921,994 A | 7/1999 | Andreas et al. |
| 5,928,252 A | 7/1999 | Steadman et al. |
| 5,947,982 A | 9/1999 | Duran |
| 5,968,050 A | 10/1999 | Torrie |
| 5,980,538 A | 11/1999 | Fuchs et al. |
| 5,984,933 A | 11/1999 | Yoon |
| 6,022,360 A | 2/2000 | Reimels et al. |
| 6,036,699 A | 3/2000 | Andreas et al. |
| 6,051,006 A | 4/2000 | Shluzas et al. |
| 6,071,289 A | 6/2000 | Stefanchik et al. |
| 6,074,403 A | 6/2000 | Nord |
| 6,096,051 A | 8/2000 | Kortenbach et al. |
| 6,136,010 A | 10/2000 | Modesitt et al. |
| 6,143,004 A | 11/2000 | Davis et al. |
| 6,156,039 A | 12/2000 | Thal |
| 6,187,011 B1 | 2/2001 | Torrie |
| 6,197,035 B1 | 3/2001 | Loubens et al. |
| 6,217,592 B1 | 4/2001 | Freda et al. |
| 6,270,503 B1 | 8/2001 | Schmieding |
| 6,296,659 B1 | 10/2001 | Foerster |
| 6,332,889 B1 | 12/2001 | Sancoff et al. |
| 6,475,135 B1 | 11/2002 | Levy |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,582,453 B1 | 6/2003 | Tran et al. |
| 6,585,730 B1 | 7/2003 | Foerster |
| 6,605,096 B1 | 8/2003 | Ritchart |
| 6,723,107 B1 | 4/2004 | Skiba et al. |
| 6,725,082 B2 | 4/2004 | Sati et al. |
| 6,770,076 B2 | 8/2004 | Foerster |
| 6,770,084 B1 | 8/2004 | Bain et al. |
| 6,802,807 B2 | 10/2004 | Anderson et al. |
| 6,855,157 B2 | 2/2005 | Foerster et al. |
| 6,878,150 B1 | 4/2005 | McGuire et al. |
| 6,893,448 B2 | 5/2005 | O'Quinn et al. |
| 6,896,686 B2 | 5/2005 | Weber |
| 6,911,034 B2 | 6/2005 | Nobles et al. |
| 6,936,054 B2 | 8/2005 | Chu |
| 6,984,237 B2 | 1/2006 | Hatch et al. |
| 6,997,932 B2 | 2/2006 | Dreyfuss et al. |
| 7,025,770 B2 | 4/2006 | McGuire et al. |
| 7,083,638 B2 | 8/2006 | Foerster |
| 7,090,686 B2 | 8/2006 | Nobles et al. |
| 7,112,208 B2 | 9/2006 | Morris et al. |
| 7,118,583 B2 | 10/2006 | O'Quinn et al. |
| 7,198,631 B2 | 4/2007 | Kanner et al. |
| 7,232,448 B2 | 6/2007 | Battles et al. |
| 7,285,124 B2 | 10/2007 | Foerster |
| 7,297,145 B2 | 11/2007 | Woloszko et al. |
| 7,329,264 B2 | 2/2008 | Merves |
| 7,377,926 B2 | 5/2008 | Topper et al. |
| 7,449,024 B2 | 11/2008 | Stafford |
| 7,544,199 B2 | 6/2009 | Bain et al. |
| 7,572,265 B2 | 8/2009 | Stone et al. |
| 7,575,578 B2 | 8/2009 | Wetzler et al. |
| 7,585,305 B2 | 9/2009 | Dreyfuss |
| 7,608,084 B2 | 10/2009 | Oren et al. |
| 7,695,494 B2 | 4/2010 | Foerster |
| 7,717,912 B2 | 5/2010 | Woloszko et al. |
| 7,722,630 B1 | 5/2010 | Stone et al. |
| 7,727,256 B2 | 6/2010 | McGregor |
| 7,758,597 B1 | 7/2010 | Tran et al. |
| 7,771,438 B2 | 8/2010 | Dreyfuss et al. |
| 7,815,654 B2 | 10/2010 | Chu |
| 7,879,046 B2 | 2/2011 | Weinert et al. |
| 7,879,048 B2 | 2/2011 | Bain et al. |
| 7,883,519 B2 | 2/2011 | Oren et al. |
| 7,922,744 B2 | 4/2011 | Morris et al. |
| 7,963,972 B2 | 6/2011 | Foerster et al. |
| 7,972,344 B2 | 7/2011 | Murray et al. |
| 8,110,000 B2 | 2/2012 | Collins |
| 8,147,505 B2 | 4/2012 | Delli-Santi |
| 8,409,225 B2 | 4/2013 | Bull |
| 8,449,552 B2 | 5/2013 | Sanders |
| 8,551,123 B2 | 10/2013 | Pandya |
| 2001/0037119 A1 | 11/2001 | Schmieding |
| 2002/0147456 A1 | 10/2002 | Diduch et al. |

(56) References Cited

U.S. PATENT DOCUMENTS

| | | |
|---|---|---|
| 2002/0173800 A1 | 11/2002 | Dreyfuss et al. |
| 2003/0078599 A1 | 4/2003 | O'Quinn et al. |
| 2003/0195528 A1 | 10/2003 | Ritchart |
| 2003/0220659 A1 | 11/2003 | Schmieding et al. |
| 2003/0233106 A1 | 12/2003 | Dreyfuss |
| 2004/0010273 A1 | 1/2004 | Diduch et al. |
| 2004/0015177 A1 | 1/2004 | Chu |
| 2004/0138682 A1 | 7/2004 | Onuki et al. |
| 2004/0249394 A1 | 12/2004 | Morris et al. |
| 2005/0165419 A1 | 7/2005 | Sauer et al. |
| 2005/0240226 A1 | 10/2005 | Foerster et al. |
| 2006/0052801 A1 | 3/2006 | Dreyfuss et al. |
| 2006/0241658 A1 | 10/2006 | Cerundolo |
| 2006/0271060 A1 | 11/2006 | Gordon |
| 2007/0060953 A1 | 3/2007 | Morris et al. |
| 2007/0118150 A1 | 5/2007 | Weber |
| 2007/0149986 A1 | 6/2007 | Morris et al. |
| 2007/0179524 A1 | 8/2007 | Weber et al. |
| 2007/0233128 A1 | 10/2007 | Schmieding et al. |
| 2008/0015594 A1 | 1/2008 | Ritchart et al. |
| 2008/0097482 A1 | 4/2008 | Bain et al. |
| 2009/0036905 A1 | 2/2009 | Schmieding |
| 2009/0062816 A1 | 3/2009 | Weber |
| 2009/0062819 A1 | 3/2009 | Burkhart et al. |
| 2009/0131956 A1 | 5/2009 | Dewey et al. |
| 2009/0222040 A1 | 9/2009 | Foerster |
| 2009/0222041 A1 | 9/2009 | Foerster |
| 2009/0318965 A1 | 12/2009 | Burkhart |
| 2010/0137889 A1 | 6/2010 | Oren et al. |
| 2010/0152752 A1 | 6/2010 | Denove et al. |
| 2010/0191283 A1 | 7/2010 | Foerster et al. |
| 2010/0249806 A1 | 9/2010 | Oren et al. |
| 2010/0268256 A1 | 10/2010 | Dreyfuss et al. |
| 2011/0009867 A1 | 1/2011 | Oren |
| 2011/0066165 A1 | 3/2011 | Skinlo et al. |
| 2011/0144647 A1 | 6/2011 | Appenzeller et al. |
| 2011/0208198 A1 | 8/2011 | Anderson et al. |

OTHER PUBLICATIONS

Coughlin, et al. "Second MTP Joint Instability: Grading of the Deformity and Description of Surgical Repair of Capsular Insufficiency" The Physician and Sportmedicine, Sep. 3, 2011, 39(3):132-141.

Blitz, et al. "*Plantar Plate Repair of the Second Metatarsophalangeal Joint: Technique and Tips*" Journal of Foot & Ankle Surgery, 2004 43(4):266-270.

Fleming and Camasta, "*Plantar Plate Dysfunction*" Chapter 4, (2002) pp. 22-28, http://www.podiatryinstitute.com/pdfs/Update_2002/2002_04.pdf.

Gregg et al., "*Plantar Plate Repair and Weil Osteotomy for Metatarsophalangeal Joint Instability*" Foot and Ankle Surgery, (2007) 13:116-121.

Nery et al., "*Lesser Metatarsophalangeal Joint Instability: Prospective Evaluation and Repair of Plantar Plate and Capsular Insufficiency*" Foot and Ankle International, Apr. 2012 33(4):301-311.

\* cited by examiner

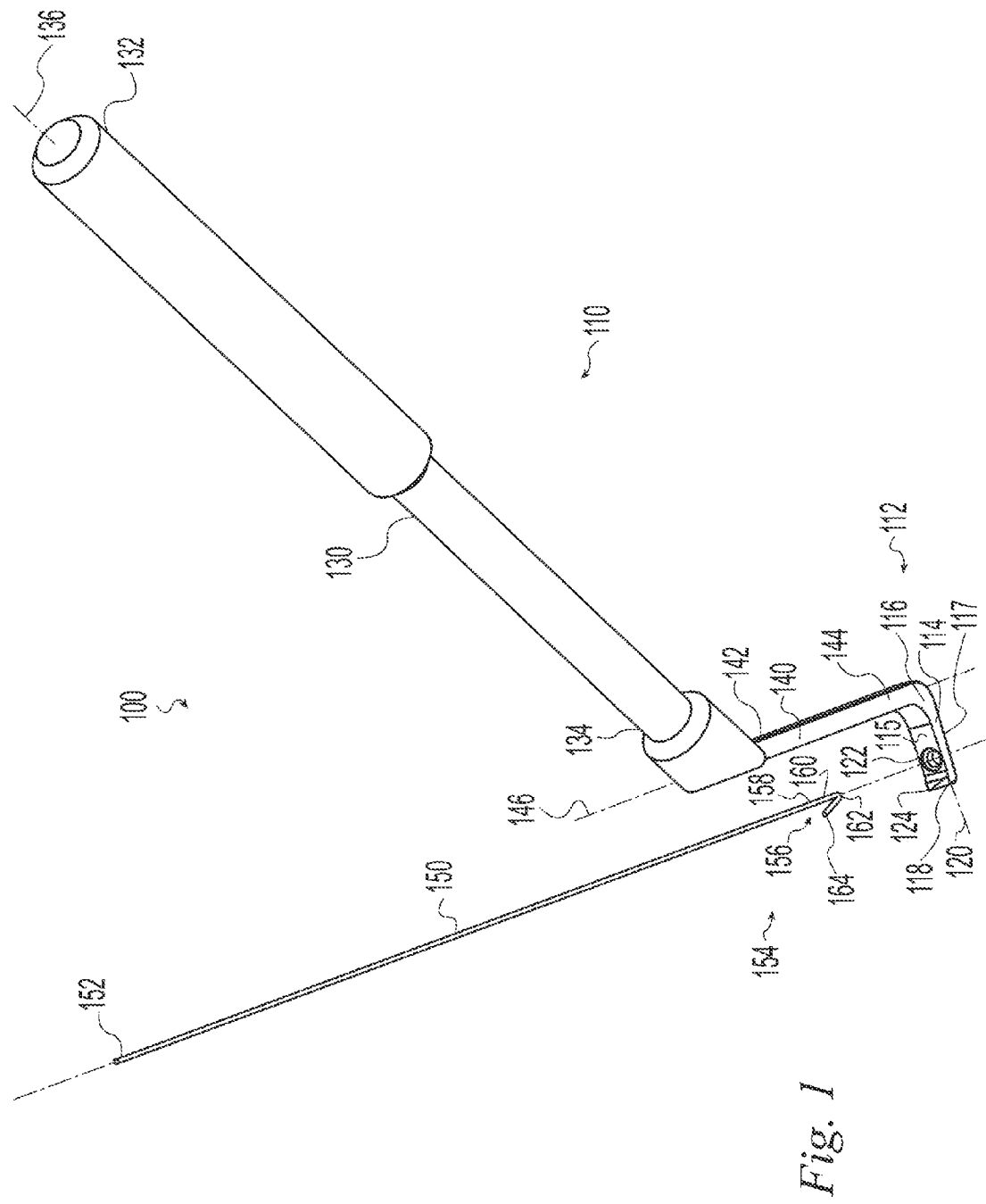

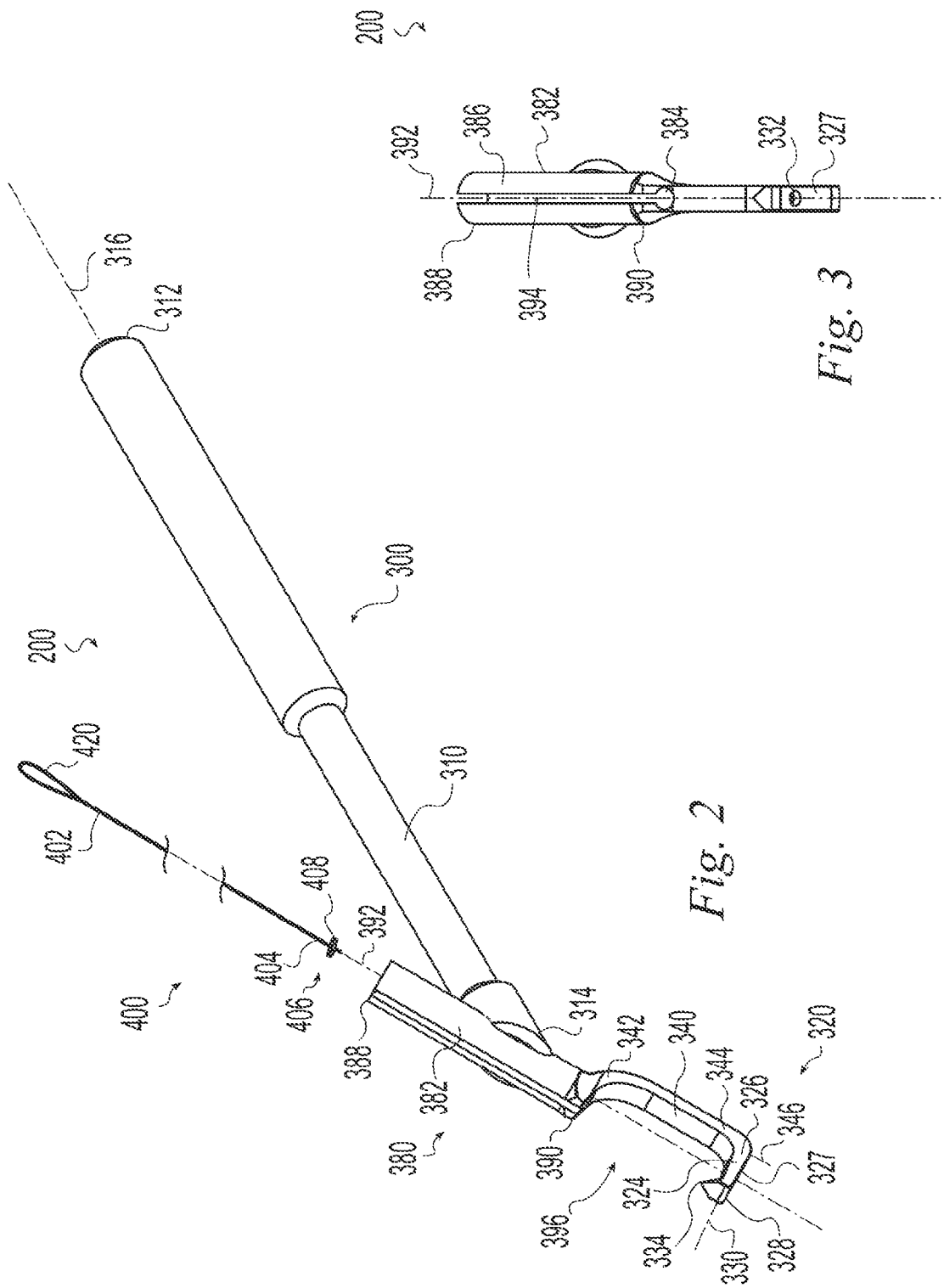

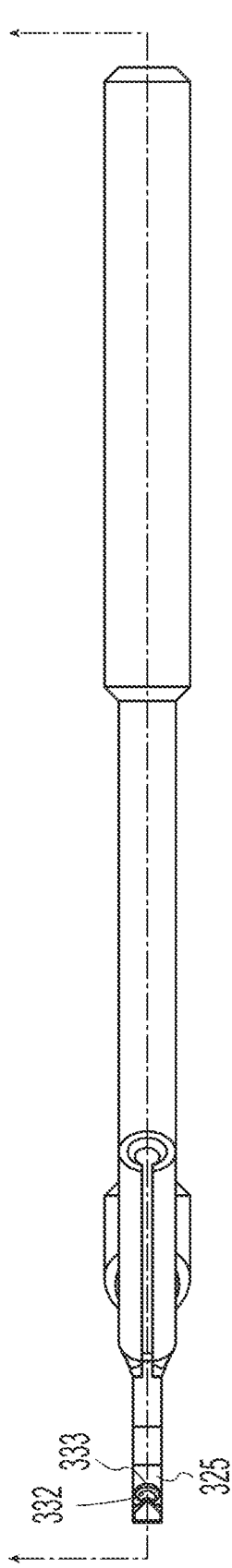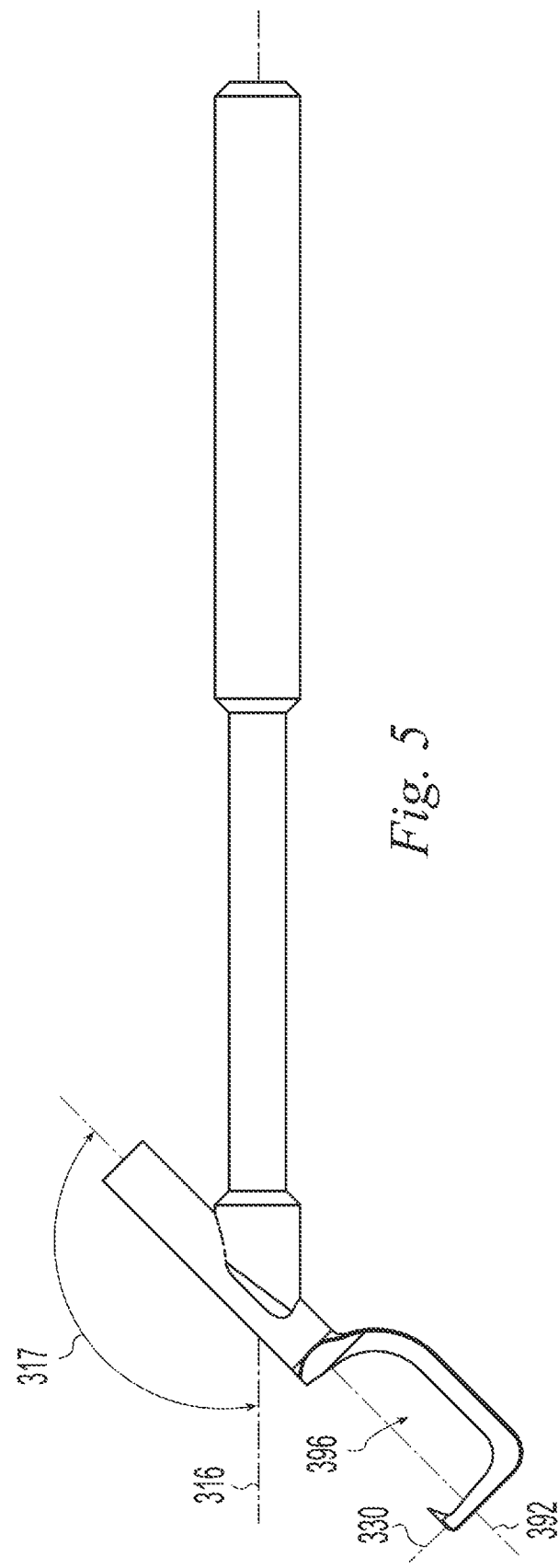
Fig. 4
Fig. 5

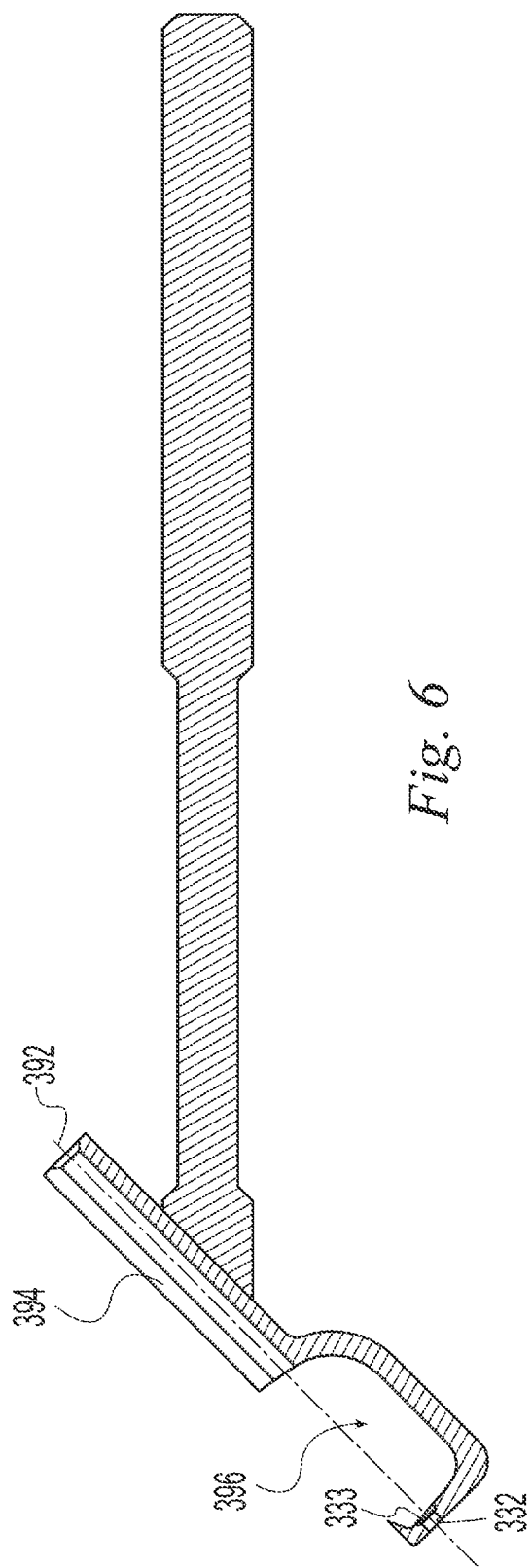

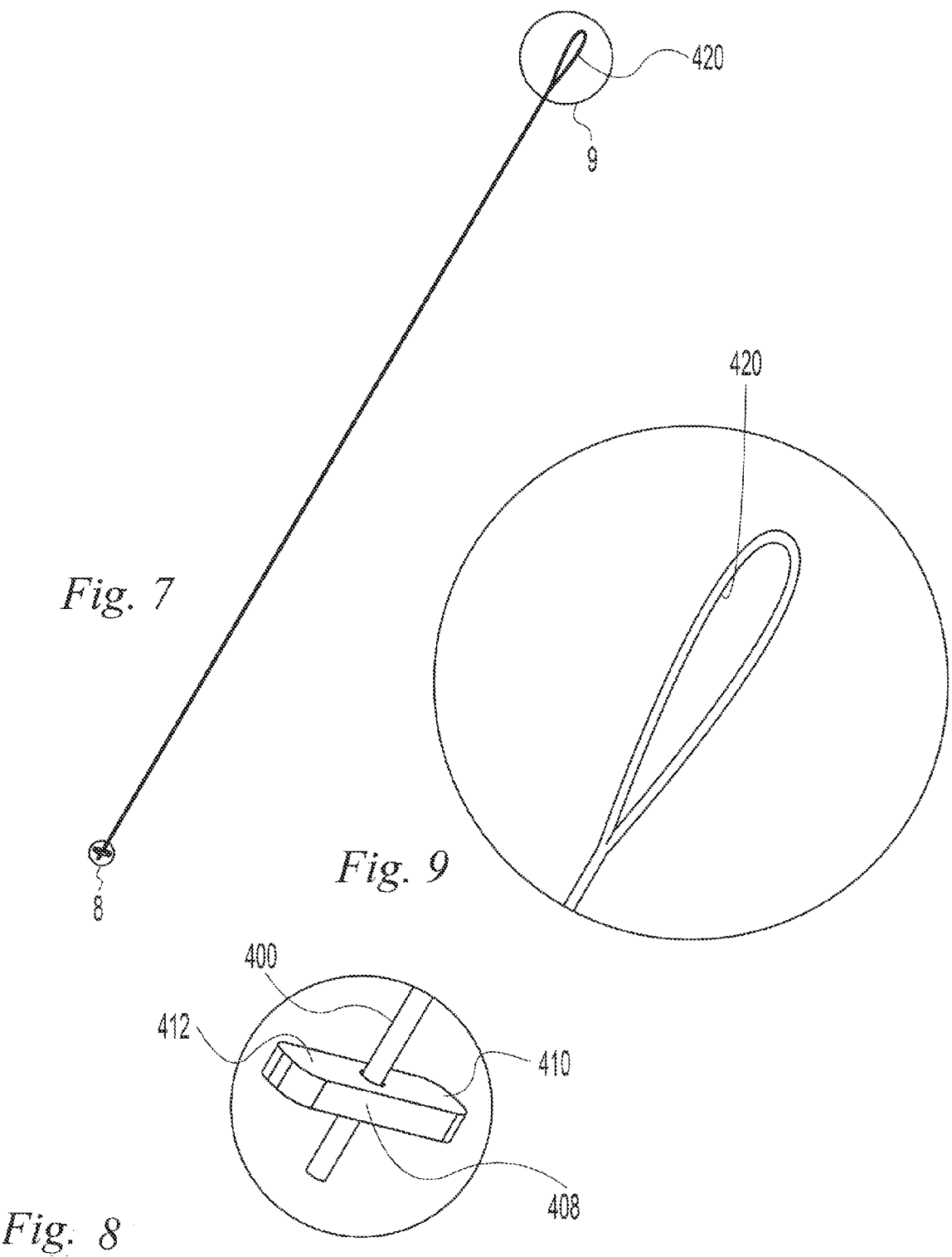

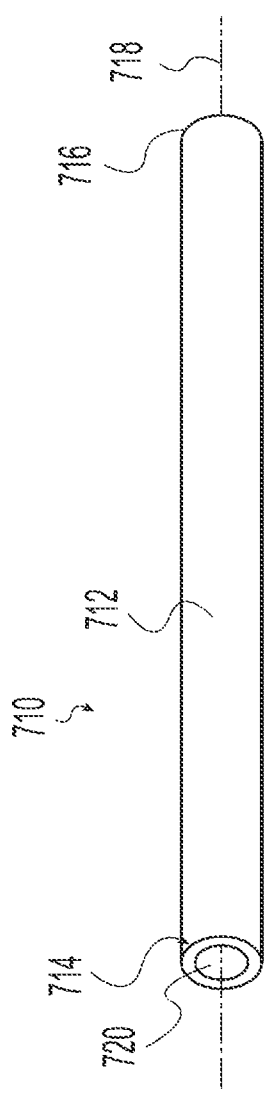
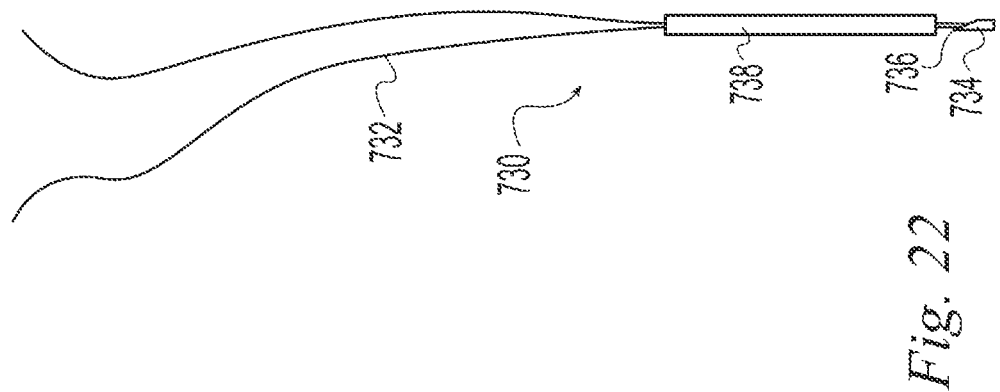
Fig. 21
Fig. 22

ORTHOPEDIC SUTURE PASSER AND METHOD

CROSS-REFERENCE TO RELATED APPLICATIONS

This application claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, U.S. Provisional Application No. 61/506,004, filed Jul. 8, 2011, all of which are herein incorporated by reference.

FIELD OF THE INVENTION

The invention relates to devices and methods to pass a suture through material such as, for example, body tissues of a surgical patient and in particular for passing a suture through a bone tunnel in an orthopedic surgical procedure.

BACKGROUND

Various conditions affecting a patient may require surgical intervention involving passing a suture for example to repair a tear, repair an incision, pass grafts, attach grafts, and anchor implants. Various suture passers have been proposed. There is a need for an improved suture passer.

SUMMARY

The present invention provides a suture passer and method to pass a suture through material during a surgical intervention.

In one aspect of the invention, a suture passer includes a suture retriever and a suture. The suture retriever includes a receiver operable to receive and retain the suture and the suture includes a portion receivable and retained by the receiver. The suture may be received and maintained by way of a stopper, adhesion, hook and loop engagement, wedging, grasping, or other suitable mechanism. For example, the receiver may include an opening and the suture may include a stopper insertable into the opening. The opening may include a hole, slot, groove, notch, or other opening. The opening may extend through a portion of the receiver to define a passage through the portion of the receiver. The stopper may include a hook, barb, pledget, knot, plug, toggle, or other stopper. The receiver may receive the stopper by resilient deformation of the stopper or receiver, by changing orientation of the stopper from a receivable orientation to a retention orientation, or by other reception mechanism. In another example, the retriever includes a movable first member mounted for movement relative to a second member and movable between a first position in which the suture is receivable between the members and a second position in which the suture is grasped by the members.

The portion of the suture receivable by the receiver may be an end of the suture, a bight of the suture, or any other portion of the suture.

In another aspect of the invention, a suture passer includes a suture retriever and a suture and the suture retriever further includes a guide for guiding the suture into engagement with the suture receiver.

In another aspect of the invention, a suture passer includes a suture retriever and a suture and the suture retriever further includes a guide for guiding a cutter to form an opening in material through which the suture is passed. The guide may include a notch, groove, eye, tube, slot, rail, or other suitable guiding member able to guide a cutter. The cutter may include a wire, drill, blade, or other suitable cutter. For example, the guide may include a tube able to receive a drill and guide it to intersect a receiver. The guide may also be able to receive the suture and guide it into engagement with the receiver. The suture passer may further include a suture inserter able to engage the suture and the guide and useable to move the suture into engagement with the receiver. For example, the suture may have insufficient columnar rigidity to allow it to be pushed into engagement with the retriever by itself. A suture inserter may be used to help advance the suture. A suture inserter may include rods, wires, tubes, or other suitable members.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is an exploded perspective view of an illustrative example of a suture passer according to the present invention;

FIG. 2 is an exploded perspective view of an illustrative example of a suture passer according to the present invention;

FIG. 3 is a front elevation view of a component of the suture passer of FIG. 2;

FIG. 4 is a top plan view of the component of FIG. 3;

FIG. 5 is a side elevation view of the component of FIG. 3;

FIG. 6 is a sectional view taken along line 6-6 of FIG. 4;

FIG. 7 is a perspective view of a component of the suture passer of FIG. 2;

FIG. 8 is an enlarged perspective view of the distal end of the component of FIG. 8;

FIG. 9 is an enlarged perspective view of the proximal end of the component of FIG. 8;

FIG. 21 is a perspective view of an optional component useable with the suture passers of FIG. 1 and FIG. 2;

FIG. 22 is a side elevation view of an alternative suture useable with the suture passers of FIG. 1 and FIG. 2;

DESCRIPTION OF THE ILLUSTRATIVE EXAMPLES

Figure 10:
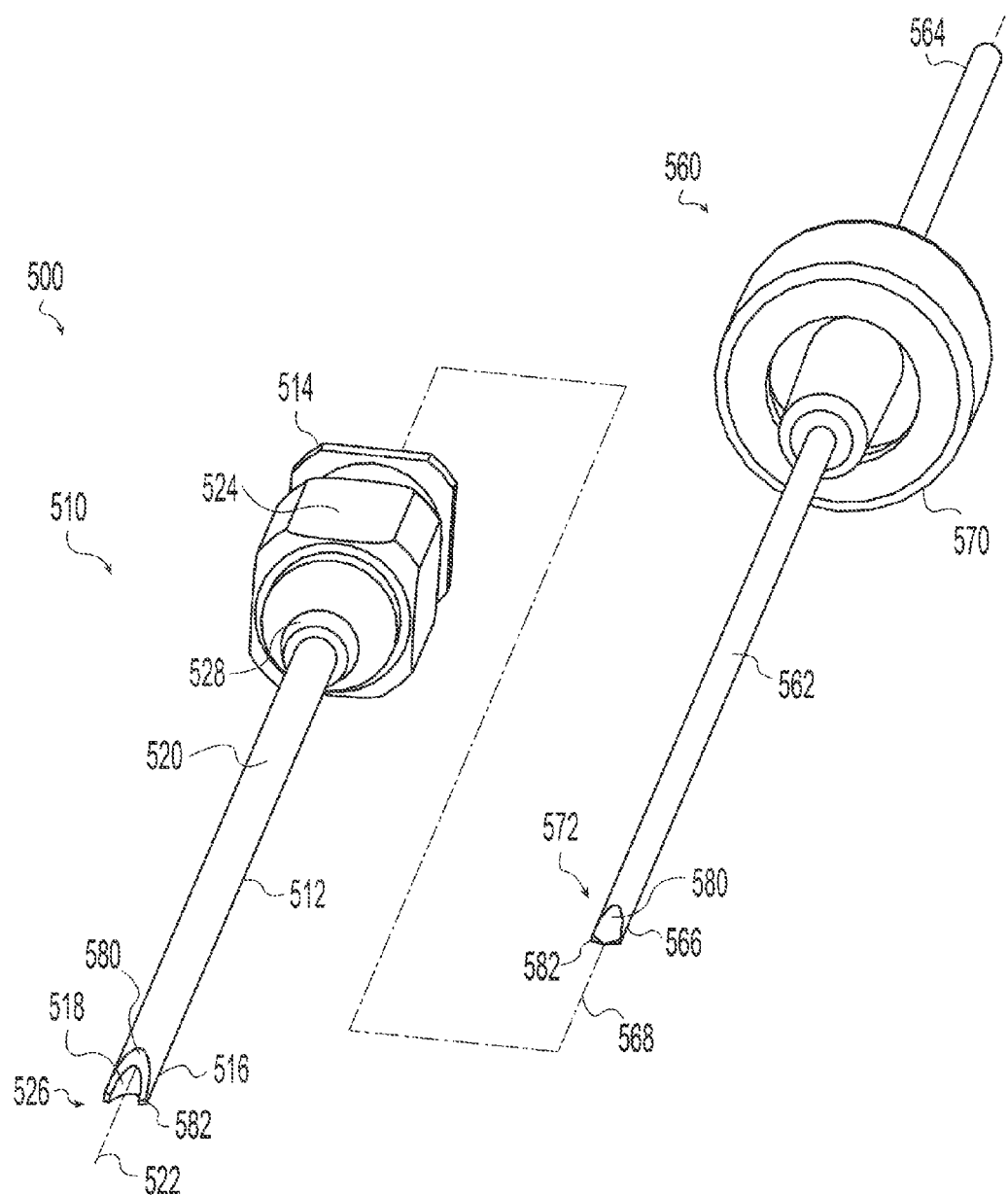
FIG. 10 is a perspective view of a drill assembly useable with the suture passer of FIG. 2.

The following illustrative examples depict instruments and techniques to pass a suture through a material. Instruments and techniques according to the present invention may be used to pass a suture through any material, at surgical sites anywhere in a patient's body, and for any purpose. Instruments and techniques according to the present invention are particularly useful to pass a suture through a bone tunnel in an orthopedic procedure. For example, it is often desirable to pass a suture through a bone tunnel which in turn is used to pass a graft into the tunnel or attach a graft in the tunnel. While suture passers in accordance with the present invention may be used with any material at any location, and in particular with any bone adjacent any joint within a patient's body, the illustrative examples are shown in use with a small bone joint such as in a hand or foot to form a tunnel in and pass a graft into a metacarpal or metatarsal bone. In particular, the illustrative examples are shown in use with a phalanx bone of the foot. The terms "suture" and "suture strand" are used herein to mean any strand or flexible member, natural or synthetic, able to be passed through material and useful in a surgical procedure. The term "material" is used herein to mean implants, grafts, fabric, tendon, ligament, fascia, skin, muscle, bone, and any other material through which it is desirable to pass a suture. The term "transverse" is used herein to mean crossing as in non-parallel. The term "bight" is used herein to mean a bend or loop formed in the intermediate portion of a suture.

FIG. 1 depicts an illustrative example of a suture passer 100. The suture passer 100 includes a suture retriever 110 and a suture 150. The retriever 110 includes a receiver 112 able to receive and retain a portion of the suture 150. In the illustrative example of FIG. 1, the receiver 112 includes a foot 114 positionable on one side of a material through which the suture is to be passed. The foot 114 has a proximal end 116, a distal end 118, a front surface 115, a back surface 117 and a longitudinal axis 120 extending between the proximal and distal ends. The foot has an opening 122 defining a passage through a portion of the receiver for receiving the suture 150 and a sharp tip 124 able to engage the material and aid in maintaining the foot 114 in a desired location. In the illustrative example of FIG. 1, the retriever 110 further includes a handle 130 having a proximal end 132, a distal end 134, and a longitudinal axis 136 extending between the proximal and distal ends. The receiver 112 may be mounted directly to the distal end 134 of the handle. In the illustrative example of FIG. 1, the receiver 112 is offset from the handle. An extension 140 having a proximal end 142, a distal end 144, and a longitudinal extension axis 146 extends away from the distal end 134 of the handle transverse to the handle axis 136. The foot 114 is mounted to the distal end 144 of the extension 140 and extends away from the extension 140 transverse to the extension axis 146.

The suture 150 includes a proximal end 152 and a distal end 154. The distal end includes a stopper 156. In the illustrative example of FIG. 1 the stopper 156 includes a hook 158 formed on the distal end 154. For example, the distal end may be bent, molded, heat set, or otherwise formed into a hook shape. The hook 158 includes a shank 160, a bend 162, and a barb 164. The hook 158 is receivable in the opening 122. As the hook 158 is advanced through the opening 122, the barb 164 and shank 160 engage the sides of the opening 122 and the barb 164 moves toward the shank 160. This movement changes the orientation of the hook to a receivable orientation in which the barb-shank maximum dimension is smaller than the opening 122 maximum dimension and the hook passes through the opening. Once the hook 158 is through the opening 122, the barb 164 springs away from the shank 160 and the hook orientation changes to a retention orientation. Pulling the hook 158 back toward the opening causes the barb 164 to engage the back surface 117 of the foot and resist withdrawal. The bend of the hook 158 is such that relatively small movement of the barb 164 is necessary for insertion of the hook through the opening 122 but relatively large movement of the barb 164, in the opposite direction, is necessary for removal. The hook 158 may be withdrawn by forcing the barb to straighten or by clipping the hook 158 off of the suture 150.

The proximal end of the suture may be unmodified or it may include a loop, knot, hook, barb, or other feature for engaging another material.

In use, the receiver 112 is positioned behind material through which the suture 150 is to be passed. The distal end 154 of the suture is advanced through the material and the stopper 156 is engaged with the receiver 112. The receiver 112 is then withdrawn from behind the material to advance the suture further and retrieve it partially or fully through the material. The suture 150 may be used to connect the material to another material. For example the suture 150 may be used to attach soft tissue to bone. The suture 150 may be used to retrieve something through the material. For example, the suture 150 may be used to retrieve a graft through a bone tunnel. In the illustrative example of FIG. 1, the foot 114 may be positioned adjacent a bone with the opening 122 aligned with a tunnel formed in the bone and the tip 124 engaged with the bone. The distal end 154 of the suture 150 may be advanced through the bone tunnel and opening 122 until the hook 158 engages the foot 114. The proximal end 152 of the suture may be secured to a graft such as by tying, stitching, looping, knotting, hooking, or other securing mechanism. The foot may then be withdrawn away from the bone tunnel to retrieve the distal 154 end of the suture and pull the graft with it. Further pulling of the suture advances the graft into the bone tunnel.

FIGS. 2-9 depict an illustrative example of a suture passer 200 similar to that of FIG. 1 and including a suture retriever 300 and a suture 400. In the illustrative example of FIGS. 2-9, the suture retriever 300 includes a handle 310, a receiver 320, and a guide 380. The handle 310 includes a proximal end 312, a distal end 314, and a longitudinal axis 316 extending between the proximal and distal ends. The receiver 320 includes a foot 324 positionable on one side of a material through which the suture is to be passed. The foot 324 has a proximal end 326, a distal end 328, a front surface 325, a back surface 327 and a longitudinal axis 330 extending between the proximal and distal ends. The foot 324 has an opening 332 having an opening axis and able to receiving the suture 400. The opening 332 includes an enlarged counterbore 333. The foot further includes a sharp tip 334 able to engage the material and aid in maintaining the foot 324 in a desired location. The receiver 320 is offset from the handle 310. An extension 340 having a proximal end 342, a distal end 344, and a longitudinal extension axis 346 extends away from the distal end 314 of the handle transverse to the handle axis 316. The foot 324 is mounted to the distal end 344 of the extension 340 and extends away from the extension 340 transverse to the extension axis 346.

The guide 380 includes a tube 382 having an inner surface 384, an outer surface 386, a proximal end 388, and a distal end 390. The inner surface 384 defines an inner diameter and a longitudinal axis 392. The tube 382 is mounted to the distal end 314 of the handle 310 with the tube axis 392 transverse to the handle axis 316 and coaxial with the opening 332 in the foot 324. The handle 310 axis 316 forms an angle 317 with the tube axis 392. The angle 317 facilitates manipulating the retriever 300 while maintaining a line of sight for the user and to prevent interference with tissues surrounding the surgical site. The angle 317 may have any suitable value. Preferably the angle 317 is in the range of 90 to 270 degrees. The handle 310 may also be mounted at any location around the circumference of the tube 382. In the illustrative embodiment of FIGS. 2-9, the handle is coplanar with the foot 324. The tube 382 includes a slot 394 through the sidewall of the tube from the inner surface 384 to the outer surface 386 and extending from the proximal end 388 to the distal end 390. The guide 380 and foot 324 define a space 396 between them for receiving a bone.

The suture 400 includes a proximal end 402 and a distal end 404. The distal end includes a stopper 406. In the illustrative example of FIGS. 2-9 the stopper 406 includes a pledget 408. The pledget 408 is mounted to the suture 400 such as by adhering, welding, crimping, molding or other suitable mounting method. The pledget 408 may also be formed as a unitary part of the suture. The pledget is resilient to allow it to bend or compress to fit through the opening 332. It may also be toggled to one side such as for example by bending the suture adjacent the pledget 408 to fit through the opening 332. In the illustrative example of FIGS. 2-9, the pledget 408 includes radially extending tabs 410, 412 that bend from substantially perpendicular to the suture 400 to substantially parallel to the suture 400 to reduce the radial dimension of the pledget 408 and allow it to pass through the opening in a receivable orientation. Once the pledget 408 is through the opening 332, the tabs 410, 412 spring back to their initial position and resume a retention orientation. The proximal end of the suture 400 includes a loop 420. The loop may be formed by tying a knot in a bight of a single or multiple strand suture 400, tying the ends of multiple strands together, splitting a monofilament strand, molding, or other suitable loop formation method. In the illustrative example of FIGS. 2-9, the loop is formed by molding a loop on a monofilament strand.

FIG. 10 illustrates a drill assembly 500 useable with the suture passer 200. The drill assembly 500 includes a drill tube 510 and an obturator 560. The drill tube 510 includes a tubular body 512 having a proximal end 514, a distal end 516, an inner surface 518, and an outer surface 520. The inner surface 518 defines an inner diameter and a longitudinal axis 522 extending between the proximal and distal ends. In the illustrative embodiment of FIG. 10, a connector 524 is mounted to the drill tube 510 near the proximal end 514. In the illustrative example of FIG. 10, the connector 524 is a female Luer-type fitting. A stop 528 extends radially outwardly from the body 512.

The obturator 560 includes an elongated body 562 having a proximal end 564, a distal end 566, and a longitudinal axis 568 extending between the proximal and distal ends. In the illustrative embodiment of FIG. 10, a connector 570 is mounted to the obturator 560 intermediate the proximal and distal ends. In the illustrative example of FIG. 10, the connector 570 is a male Luer-type fitting. The obturator 560 is receivable in the drill tube 510 by inserting the distal end 566 of the obturator 560 into the proximal end 514 of the drill tube 510 and advancing the obturator until the connectors engage. The obturator 560 and drill tube 510 are locked together by rotating the connectors relative to one another. The drill tube 510 and obturator 560 have drilling tips 526, 572 that align when the obturator is inserted into the drill tube and locked. For example, the drilling tips 526, 572 may be formed by assembling the obturator 560 and drill tube 510, locking them together, and then grinding the cutting tips on the drill tube 510 and obturator 560 simultaneously. In the illustrative example of FIG. 10, when the drill tube 510 and obturator 560 are assembled, the drilling tips 526, 572 form a diamond drill tip having primary bevels 580 formed on opposed first and second sides and secondary bevels 582 to provide relief and improve cutting. The outer diameter of the drill tube 510 and the counterbore 333 of the opening 332 are sized so that the drill tube 510 may be received in the counterbore 333.

Figure 11:
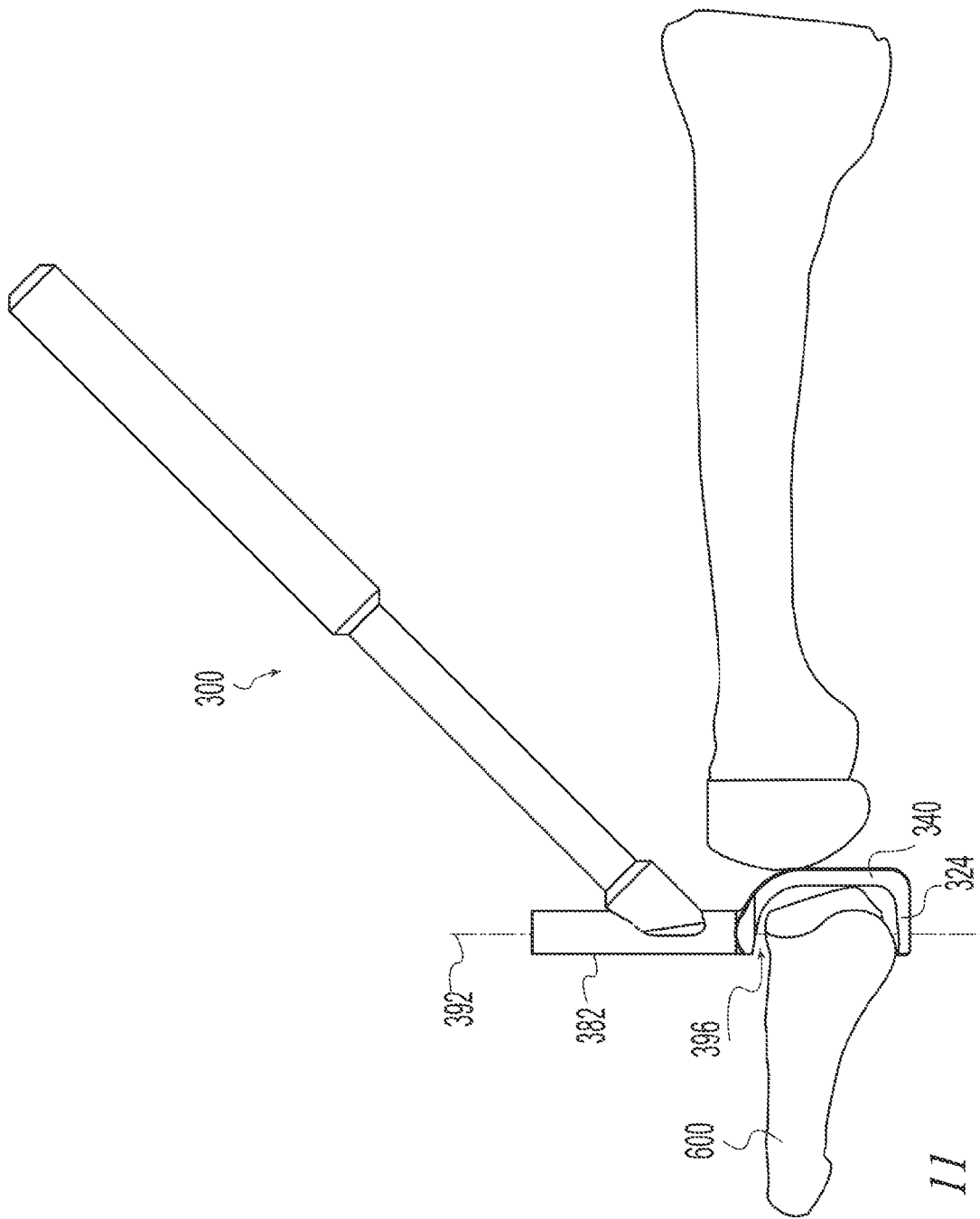
FIGS. 11-20 are side elevation views illustrating the suture passer of FIG. 2 in use.

FIGS. 11-20 illustrate the illustrative suture passer 200 of FIGS. 2-9 and the illustrative drill assembly of FIG. 10 in use to form a bone tunnel and load a graft into the tunnel. In FIG. 11, the suture retriever 300 has been positioned adjacent a bone 600 with the foot 324 on one side of the bone with the opening 332 aligned with a desired exit location for a bone tunnel and the guide axis 392 aligned with the desired tunnel axis. By viewing through the tube 382 along the axis 392, the location of the tunnel entrance can be visualized. The retriever 300 is shown positioned adjacent a phalanx bone with the extension 340 in the joint space and the guide positioned to form a tunnel from dorsal to plantar through the proximal phalanx. The guide may be positioned at any location around the joint to create bone tunnels at any desired location in the phalanx or the metatarsus. For example, the guide may be positioned to create tunnels for repairing or replacing a proper collateral ligament, accessory plantar ligament, plantar plate, or other structure in or around the joint.

Figure 12:
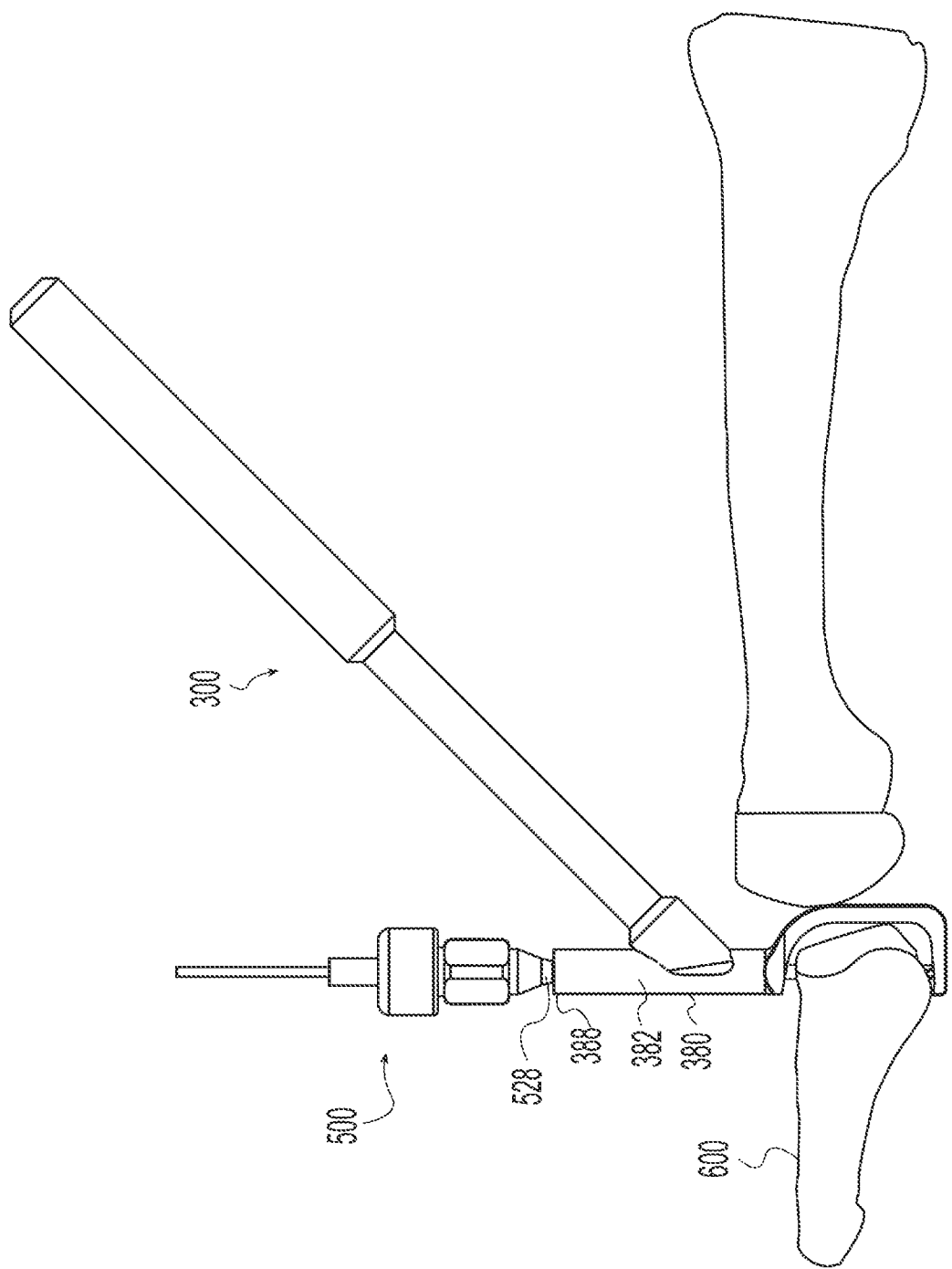

In FIG. 12, the drill assembly 500 has been guided via the inner surface 384 of the guide tube 382 to form a tunnel through the bone 600. Stop 528 abuts the proximal end 388 of the guide 380 to limit the drilling depth. In the illustrative examples of FIGS. 2-10, the stop 528 abuts the proximal end 388 when the drill tube 510 is received in the counterbore 333. Alternatively, the opening in the foot may be sized to engage the tip of the drill to limit the depth or a depth stop may be omitted.

Figure 13:
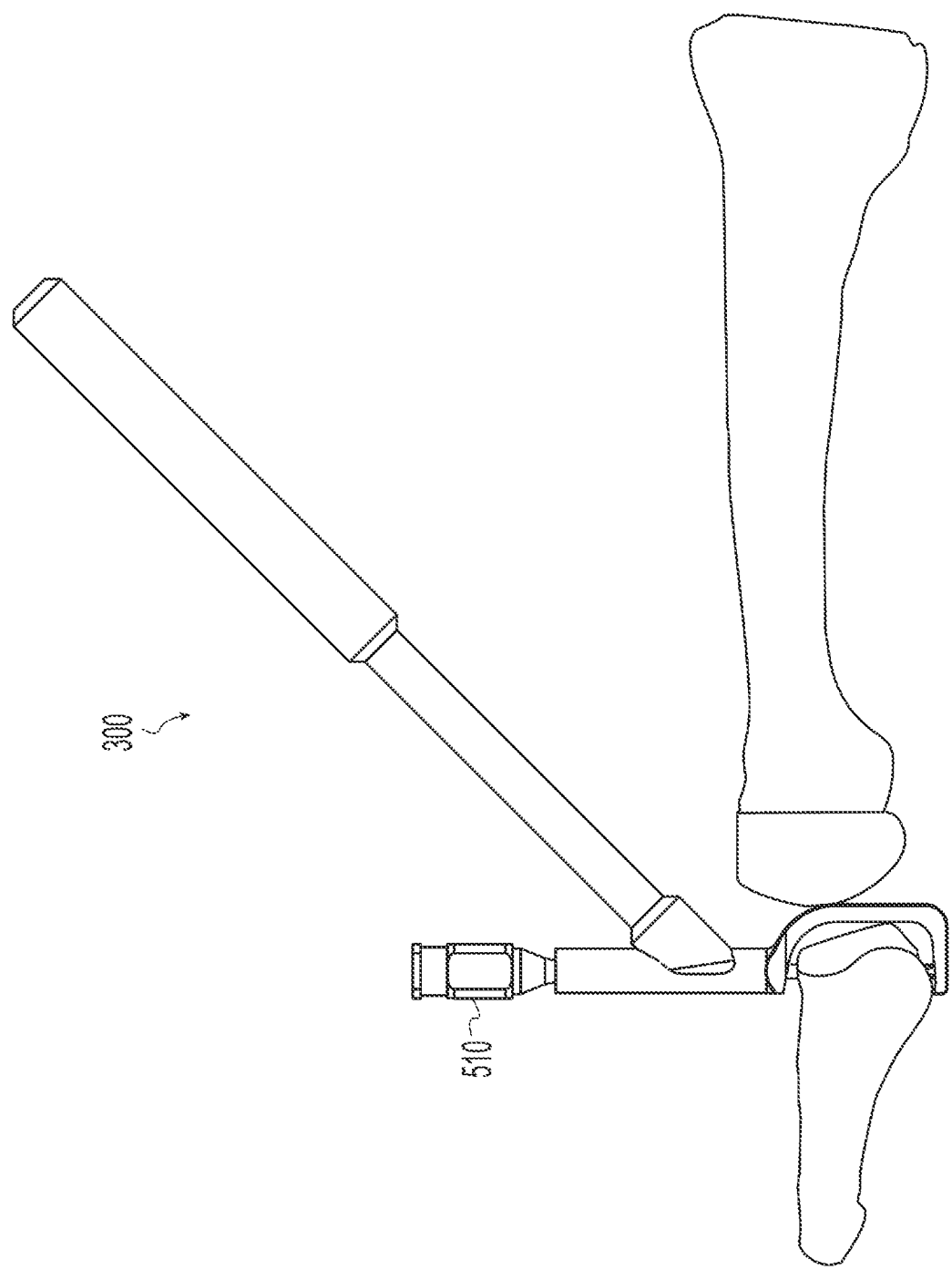

In FIG. 13, the obturator 560 has been removed leaving the drill tube 510 in place. Optionally, the drill tube 510 could be removed or a one-piece drill could be substituted for the drill assembly 500. However, by leaving the drill tube 510 in place, the drill tube 510 locks the retriever 300 in place on the bone, provides guidance for the suture, and provides a smooth passage for the suture.

Figure 14:
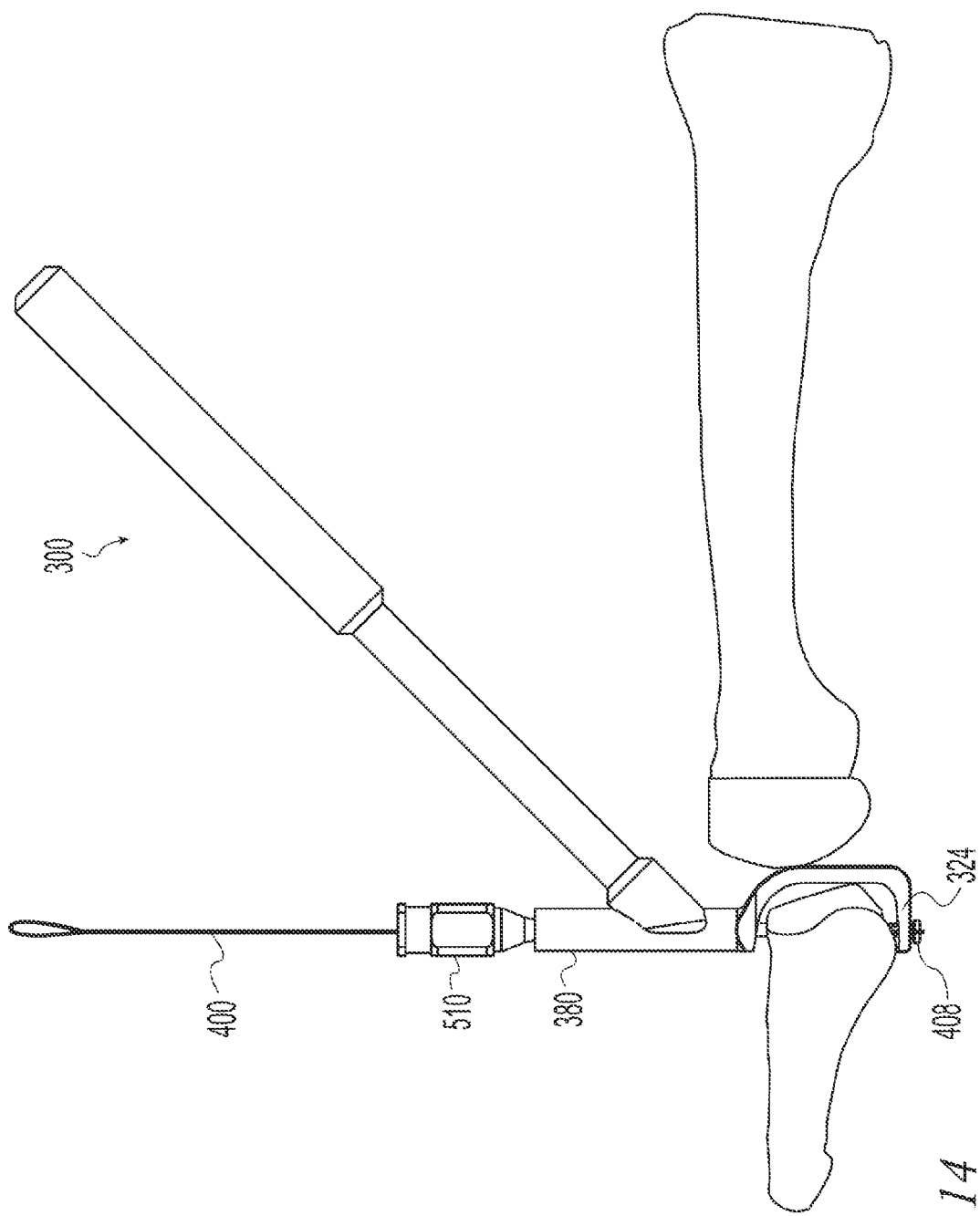

In FIG. 14, the suture 400 has been inserted until the stopper 406 engages the receiver 320. In the example of FIG. 14, the pledget 408 has been forced through the opening 332 in the foot 324.

Figure 15:
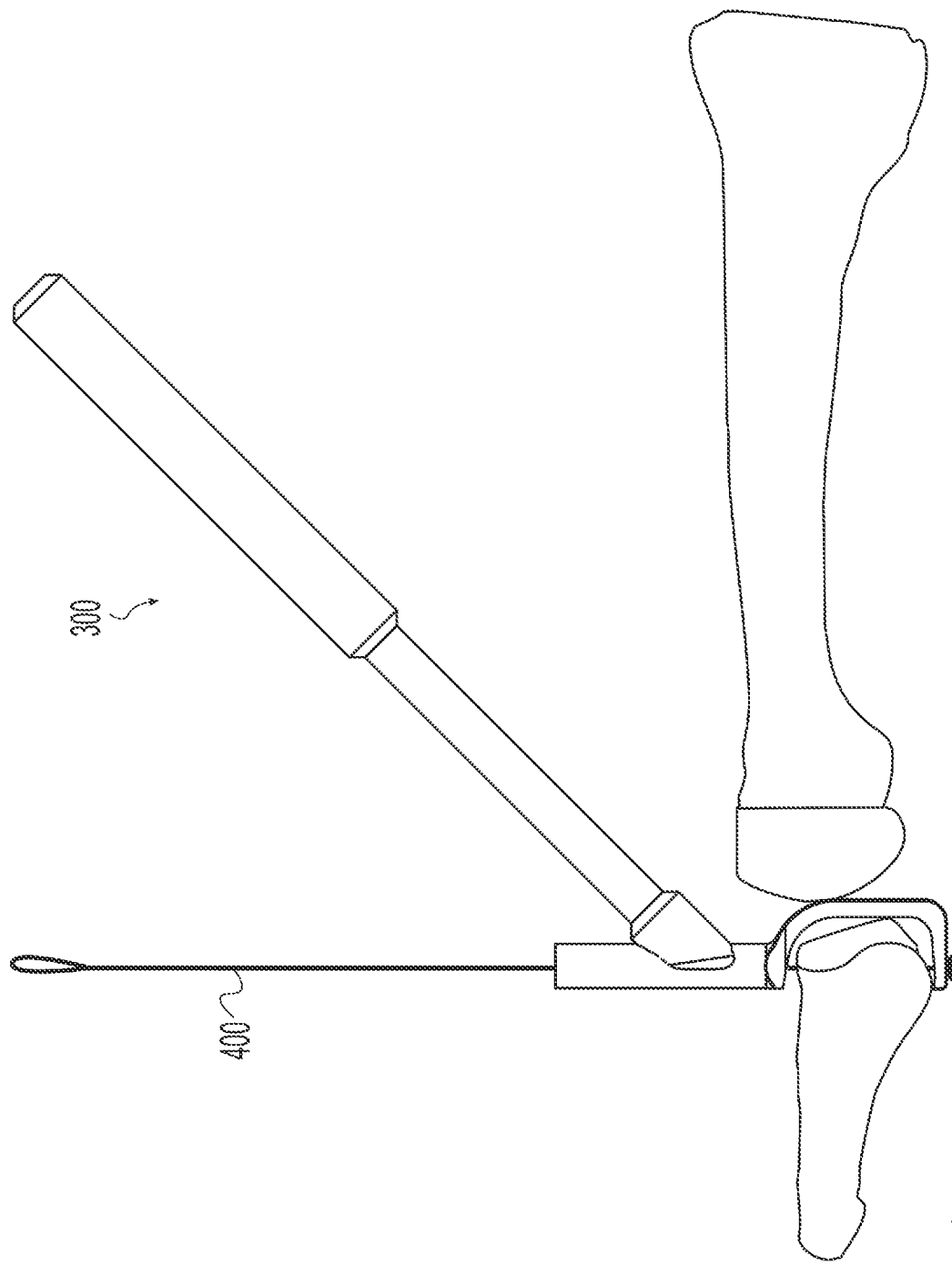

In FIG. 15, the drill tube 510 has been removed leaving the suture 400 in place.

Figure 16:
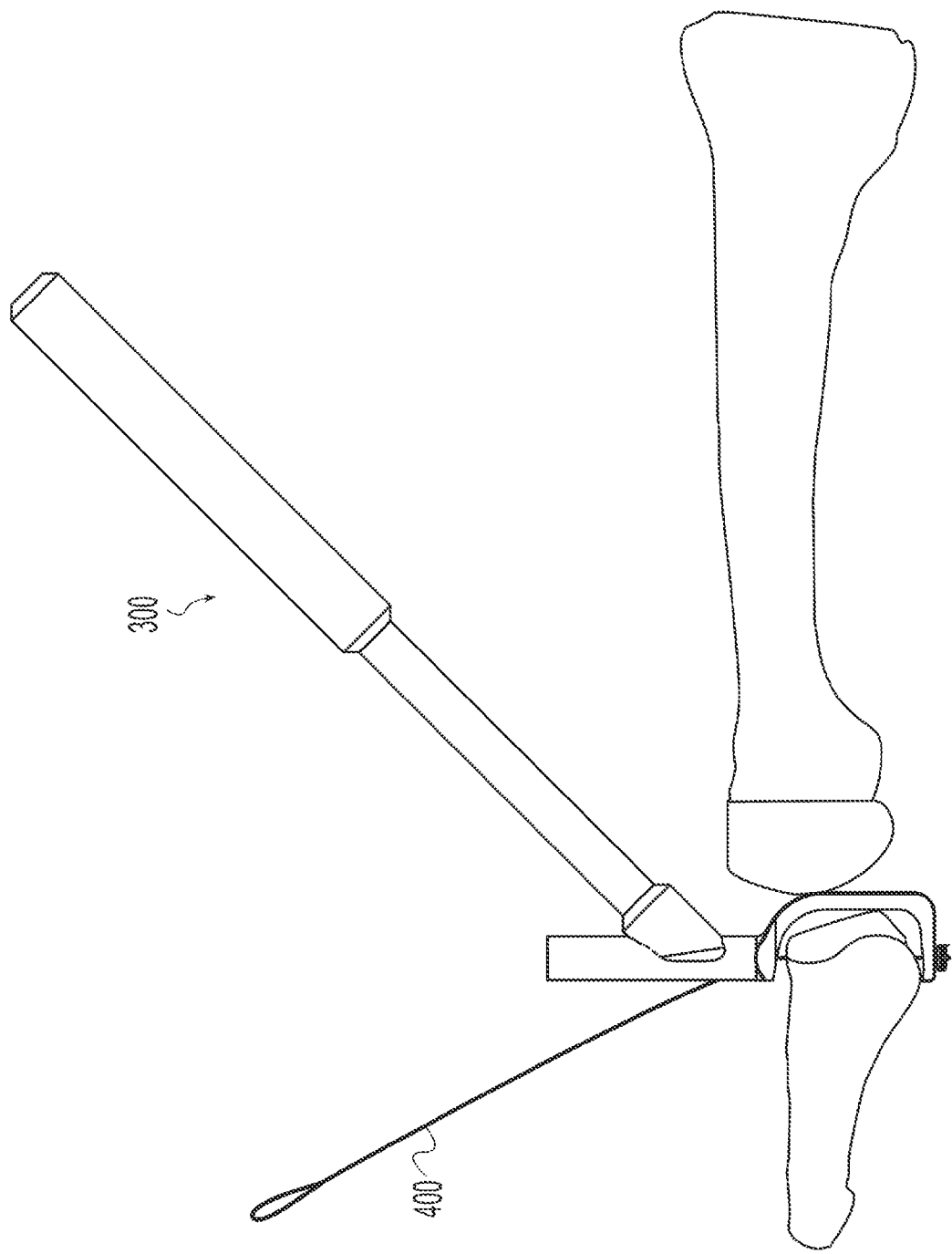

In FIG. 16, the suture 400 has been pulled through the slot 394 to free the proximal end 402 from the guide tube 382. The slot 394 simplifies withdrawing the retriever 300 from the surgical site. However, the slot 394 may be omitted and the proximal end 402 of the suture threaded through the guide tube 382 as the retriever 300 is withdrawn.

Figure 17:
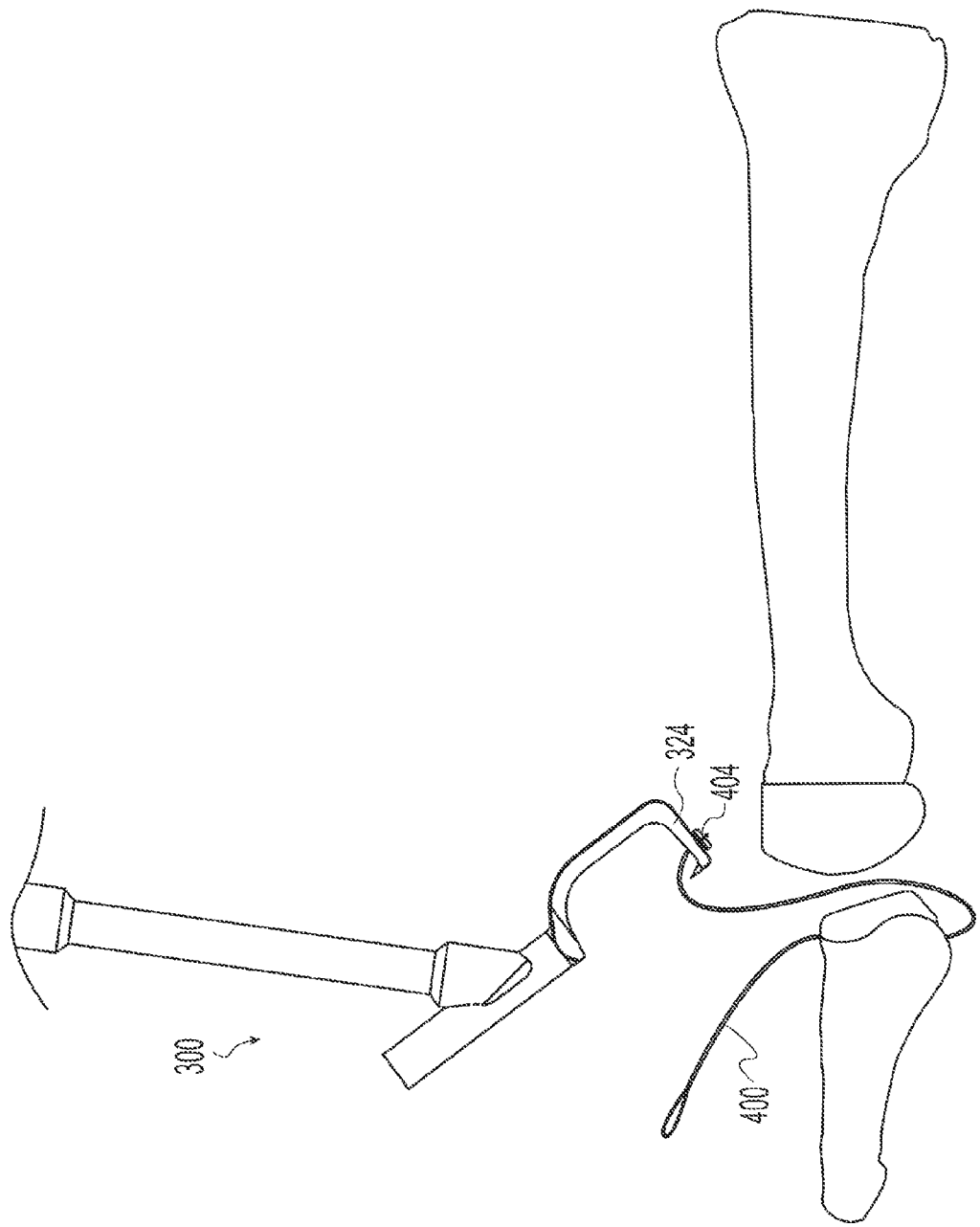

In FIG. 17, the retriever 300 has been withdrawn from the surgical site taking the distal end 404 of the suture 400 with it and thereby further advancing the suture 400 into the bone tunnel. The suture 400 may be left attached to the retriever 300 or it may be separated from the retriever by pulling the distal end 404 back through the foot or cutting off the distal end 404 of the suture.

Figure 18:
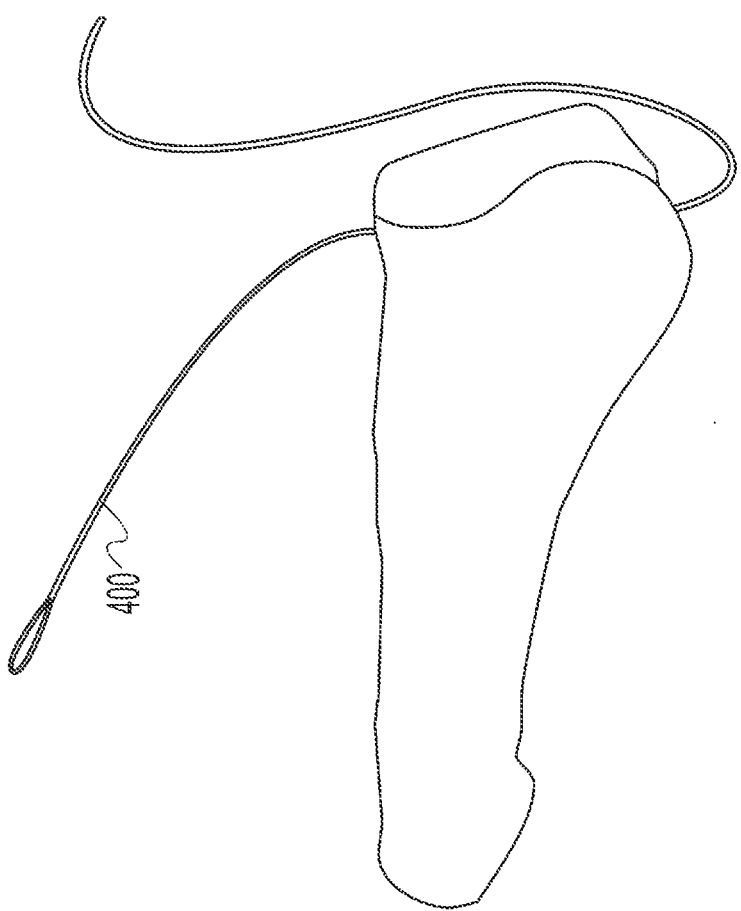

In FIG. 18, the distal end 404 of the suture 400 has been cut off to free it from the retriever 300 and the retriever 300 removed.

Figure 19:
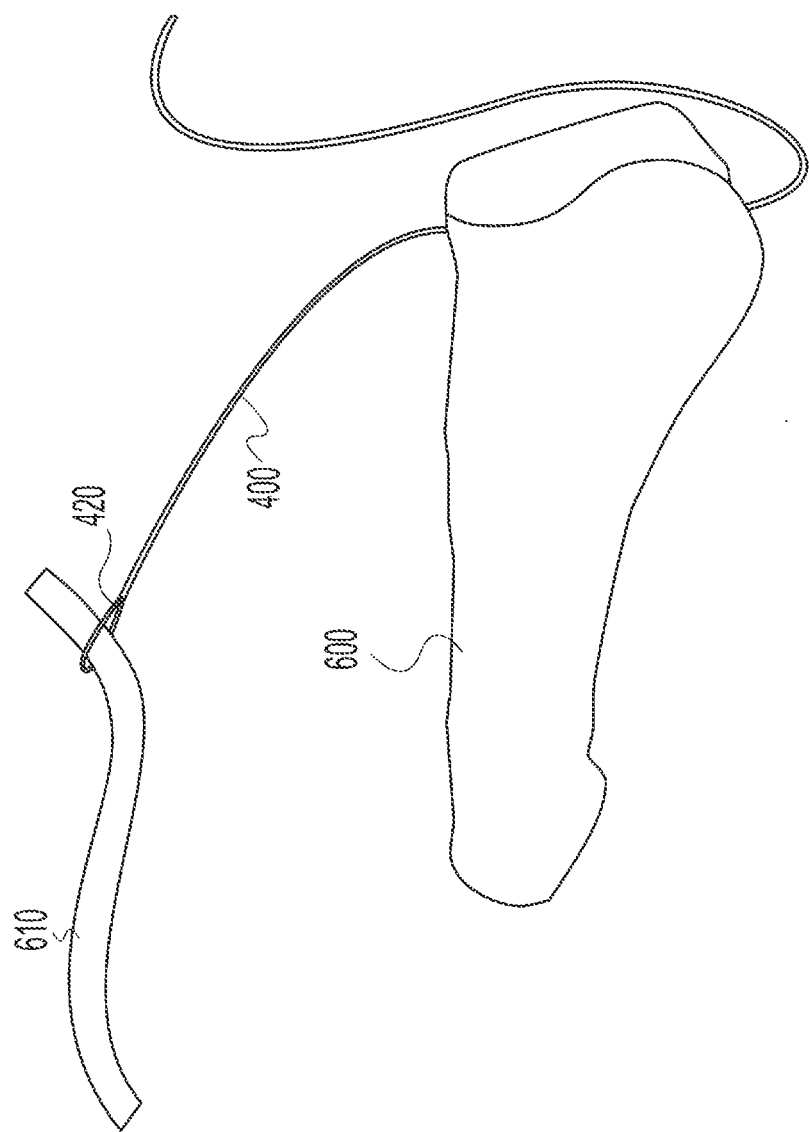

In FIG. 19, a graft 610 has been engaged with the proximal end 402 of the suture 400 by threading it through the loop 420. Alternatively, a graft or any other material may be attached to the distal end for pulling in the opposite direction. In addition to being used to retrieve a graft, the suture 400 may be used as a definitive suture in a repair or reconstruction. Also, the suture 400 may be used to pull another graft retrieval strand such as, for example, a larger or more flexible strand.

Figure 20:
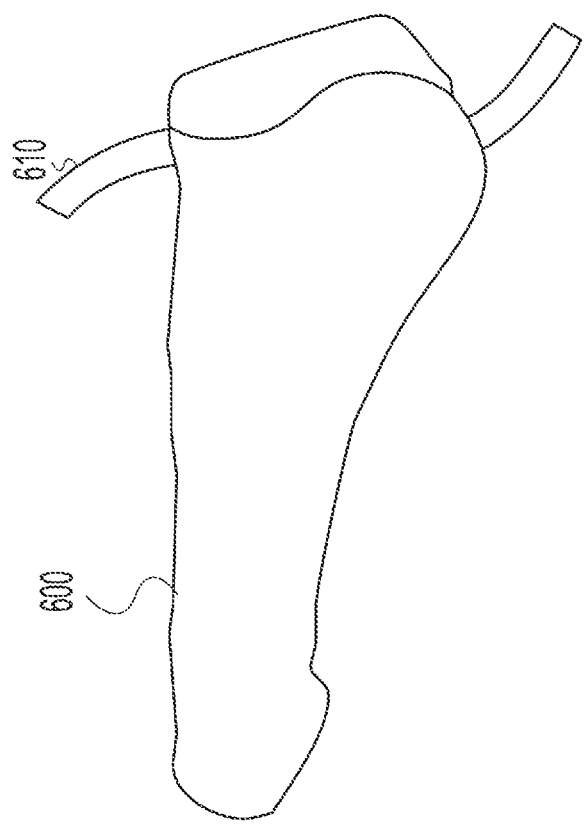

In FIG. 20, the suture 400 has been pulled to advance it through the bone tunnel and pull the graft 610 along with it to position the graft 610 in the bone tunnel and the suture 400 has been removed.

FIG. 21 illustrates a suture inserter 710 having an elongated body 712 with a proximal end 714, a distal end 716, and a longitudinal axis 718. The suture inserter 710 may be used to advance the suture 400 into engagement with the receiver 320 by pushing the stopper 406. The suture inserter 710 or the suture inserter 710 in combination with the suture may have a higher columnar strength than the suture alone and facilitate advancing the suture 400. In the illustrative example, the suture inserter includes a longitudinal passage 720 for receiving the suture 400 with the stopper 406 adjacent the distal end 716.

FIG. 22 illustrates a suture 730 having two strands 732 joined to a stopper 734 having a proximal end 736 formed at an angle to the suture strands 732 so that the proximal end 736 will hook onto the retriever 320. The suture 730 is also shown with the suture inserter 710 of FIG. 21 useable to push the stopper 734. For use in passing a graft, the suture strands 732 may be tied to form a loop, stitched to the graft, wrapped around the graft, or otherwise connected to the graft. The suture ends may also be used directly to attach hard or soft tissue, implants, or other materials at a surgical site. The suture strands may also be used directly as a ligament or tendon replacement.

Figure 23:
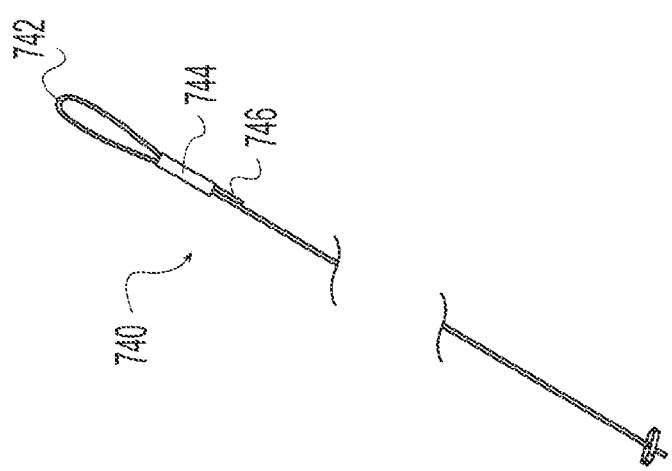
FIG. 23 is a side elevation view of an alternative suture useable with the suture passers of FIG. 1 and FIG. 2.

FIG. 23 illustrates a suture 740 having a loop 742 retained by swaging a ferrule 744 to retain the proximal end 746 of the suture 740.

Figure 24:
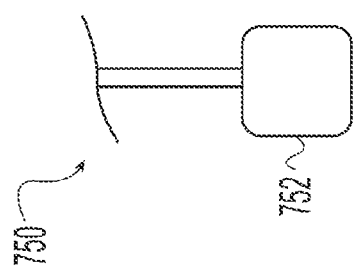
FIG. 24 is a side elevation view of an alternative stopper useable with the sutures of FIG. 1 and FIG. 2.

FIG. 24 illustrates a suture 750 having a stopper 752 formed of a block of resilient material such as, for example, a closed cell foam.

Figure 25:
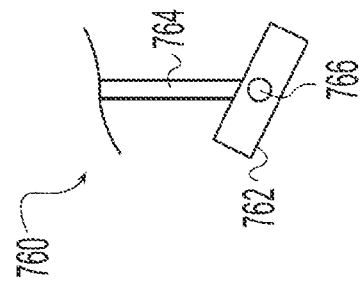
FIG. 25 is a side elevation view of an alternative stopper useable with the sutures of FIG. 1 and FIG. 2.

FIG. 25 illustrates a suture 760 having a stopper 762 joined to a strand 764 at a pivot 766 so that the stopper 762 can toggle between a receiving position generally more parallel to the strand 764 and a retaining position generally more perpendicular to the strand 764.

Figure 26:
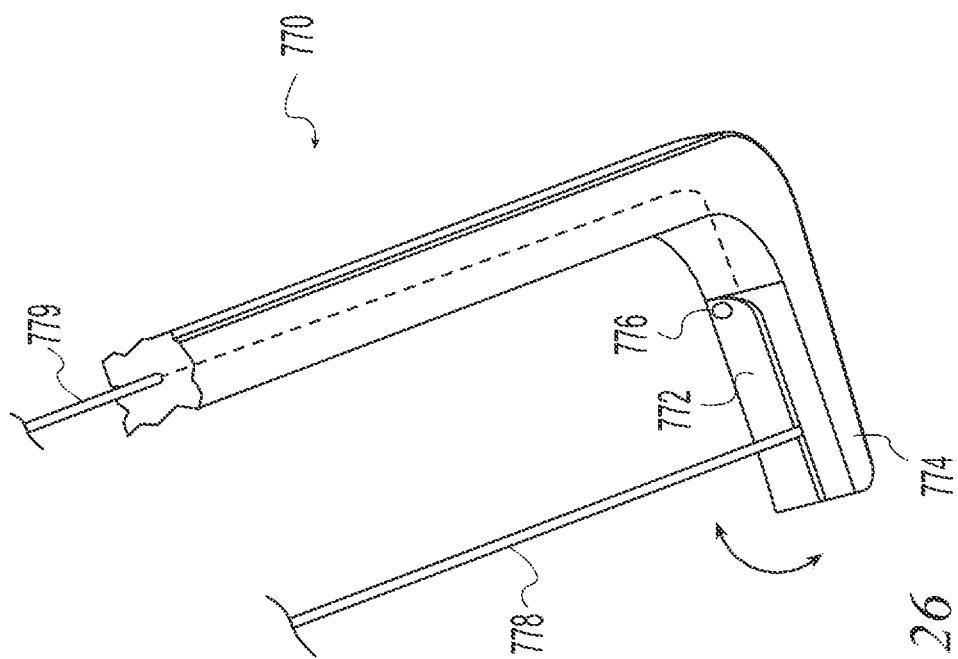
FIG. 26 is a perspective view of an alternative receiver useable with the suture passers of FIG. 1 and FIG. 2.

FIG. 26 illustrates an alternative foot 770 to the foot 224 of FIG. 2. The foot 770 has first and second opposable jaws 772, 774. The first jaw 772 is mounted for rotation relative to the second jaw about a pivot 776. The jaws 772, 774 are moveable between a first closed, position (shown) in which the jaw faces are adjacent one another and a second, open position (not shown) in which the first jaw 772 is pivoted away from the second jaw 774 to create a space between the jaws 772, 774 for receiving a suture 778. The jaws may be closed on the suture 778 to retain the suture and allow it to be retrieved. Any suitable mechanism may be used to move the first jaw relative to the second jaw. For example, a control cable 779 may be mounted in the foot and moveable by a remote actuator to move the first jaw 772 between the first and second positions.

Figure 27:
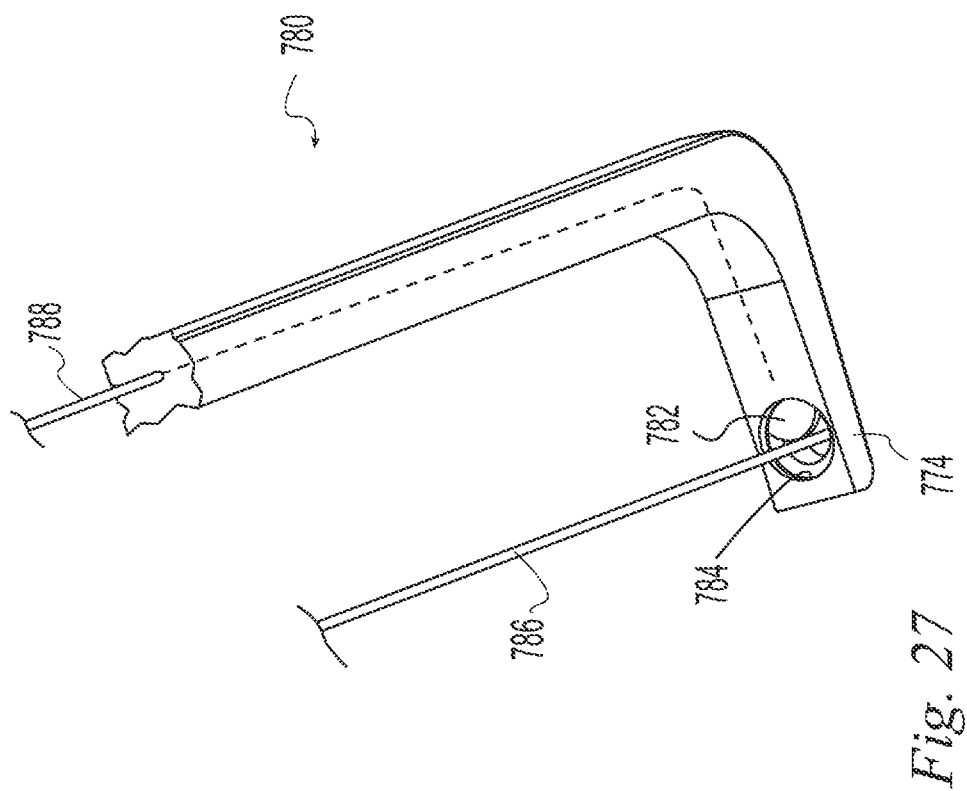
FIG. 27 is a perspective view of an alternative receiver useable with the suture passers of FIG. 1 and FIG. 2.

FIG. 27 illustrates an alternative foot 780 to the foot 224 of FIG. 2. The foot 780 has moveable member 782 mounted for movement relative to an opening 784 between a first position in which the opening is not blocked and a suture 786 may be received in the opening and a second position in which the member 782 and edge of the opening 784 grasp the suture. Any suitable mechanism may be used to move the member 782. For example, a control cable 788 may be mounted in the foot and moveable by a remote actuator to move the member 782 between the first and second positions.

The illustrative examples have shown the suture passer 200 in use to pass a suture used to pull a graft into a tunnel. However, a suture passed by the suture passer may be used in any way that sutures are known to be used. For example a suture may be used as a shuttle for pulling another suture, graft, or anything else from bottom to top rather than from top to bottom as depicted in the illustrative examples. Single strands, double strands, or any number of strands may be passed. Likewise one or more loops may be passed. Any of these may be used as a definitive suture in a repair or reconstruction, as a shuttle for pulling another material into a desired position, or for any other purpose.

Illustrative examples of instruments and methods have been shown in use to pass suture through material and to pass a graft through the material. The present invention is not limited to the specific instruments and methods depicted.

What is claimed is:

1. A suture passer comprising:
   a suture retriever having a receiver and a guide aligned with the receiver along a guide axis, the receiver being operable to receive and retain a suture and the guide being operable to guide a suture into engagement with the receiver, the receiver and guide being spaced apart and defining a bone receiving space therebetween, the retriever being operable to receive a bone in the space between the receiver and the guide; and
   a suture having a receivable portion receivable and retainable by the retainer; wherein the receiver includes an opening coaxial with the guide axis and the receivable portion of the suture includes a stopper insertable into the opening; and wherein the stopper is deformable to fit through the opening and resiliently expand after passing through the opening.

2. A suture passer comprising:
   a suture retriever having a receiver and a guide aligned with the receiver along a guide axis, the receiver being operable to receive and retain a suture and the guide being operable to guide a suture into engagement with the receiver, the receiver and guide being spaced apart and defining a bone receiving space therebetween, the retriever being operable to receive a bone in the space between the receiver and the guide; and
   a suture having a receivable portion receivable and retainable by the retainer; wherein the receiver includes an opening coaxial with the guide axis and the receivable portion of the suture includes a stopper insertable into the opening; and wherein the opening has an opening axis and the stopper is movable between a first orientation able to pass through the opening along the opening axis and a second orientation unable to pass through the opening along the opening axis.

3. A suture passer comprising:
   a suture retriever having a receiver and a guide aligned with the receiver along a guide axis, the receiver being operable to receive and retain a suture and the guide being operable to guide a suture into engagement with the receiver, the receiver and guide being spaced apart and defining a bone receiving space therebetween, the retriever being operable to receive a bone in the space between the receiver and the guide; and
   a suture having a receivable portion receivable and retainable by the retainer; wherein the receiver includes first and second opposed members, the first member being mounted for movement relative to the second member between a first position in which the members are spaced apart and able to receive the suture therebetween and a second position in which the members are close together and able to grip the suture.

4. A suture passer comprising:
   a suture retriever having a receiver and a guide aligned with the receiver along a guide axis, the receiver being operable to receive and retain a suture and the guide being operable to guide a suture into engagement with the receiver, the receiver and guide being spaced apart and defining a bone receiving space therebetween, the retriever being operable to receive a bone in the space between the receiver and the guide; and a suture having a receivable portion receivable and retainable by the retainer; wherein the receiver includes an opening coaxial with the guide axis and the receivable portion of the suture includes a stopper insertable into the opening; and further comprising a cutter engageable with the guide, the guide being operable to guide the cutter along the guide axis to form a tunnel in a bone positioned in the space between the guide and receiver.

5. The suture passer of claim 4 wherein the cutter comprises a hollow drill sleeve and an obturator removably receivable within the drill sleeve.

6. The suture passer of claim 5 wherein the drill sleeve is receivable within the opening in the receiver and the drill sleeve further includes a stop abuttable with a portion of the guide to limit the travel of the drill sleeve along the guide axis.

7. The suture passer of claim 5 wherein the drill sleeve and obturator have complimentary cutting surfaces that align when the obturator is received in the drill sleeve.

8. A suture passer comprising:
 a suture retriever having a receiver and a guide aligned with the receiver along a guide axis, the receiver being operable to receive and retain a suture and the guide being operable to guide a suture into engagement with the receiver, the receiver and guide being spaced apart and defining a bone receiving space therebetween, the retriever being operable to receive a bone in the space between the receiver and the guide; and
 a suture having a receivable portion receivable and retainable by the retainer; wherein the guide comprises an elongated tubular member having a proximal end, a distal end, and a side wall defining an inner surface and an outer surface, the guide further having a slot formed through the guide wall from the inner surface to the outer surface and from the proximal end to the distal end.

9. A method comprising:
 positioning a receiver of a suture retriever at a first position on a bone adjacent a bone joint;
 forming a tunnel through the bone;
 passing a first portion of a suture through the bone until the first portion of the suture is received by the receiver;
 retaining the first portion with the receiver; and
 moving the receiver away from the first position to advance the suture into the bone;
  wherein the suture retriever further includes a guide aligned with the receiver and
  wherein forming a tunnel through the bone comprises guiding a cutter with the guide to form the tunnel; and
  wherein the cutter comprises a drill having a hollow drill tube and an obturator receivable coaxially in the drill tube and further wherein forming a tunnel comprises driving the drill tube and obturator together into the bone and receiving a portion of the drill tube in the receiver.

10. The method of claim 9 further comprising removing the obturator while the drill tube remains in the bone and receiver.

11. A method comprising:
 positioning a receiver of a suture retriever at a first position on a bone adjacent a bone joint;
 forming a tunnel through the bone;
 passing a first portion of a suture through the bone until the first portion of the suture is received by the receiver;
 retaining the first portion with the receiver; and
 moving the receiver away from the first position to advance the suture into the bone; wherein passing a first portion of a suture through the bone comprises passing the first portion of the suture through a drill tube.

12. The method of claim 11 wherein the first portion of the suture includes a stopper and the stopper is received by the receiver.

13. The method of claim 12 wherein the receiver includes a passage and the method further comprises passing the stopper through the passage causing it to compress as it passes through the passage and then expand once it has passed all the way through the passage.

14. The method of claim 12 wherein the receiver includes a passage and the method further comprises orienting the stopper in first orientation and passing the stopper through the passage and orienting the stopper in a second orientation to prevent the stopper from passing back through the passage.

15. A method comprising:
 positioning a receiver of a suture retriever at a first position on a bone adjacent a bone joint;
 forming a tunnel through the bone;
 passing a first portion of a suture through the bone until the first portion of the suture is received by the receiver;
 retaining the first portion with the receiver; and
 moving the receiver away from the first position to advance the suture into the bone;
 attaching the suture to a graft; and
 pulling the graft into the bone tunnel.

\* \* \* \* \*